US010500063B2

(12) United States Patent
Skolnick et al.

(10) Patent No.: US 10,500,063 B2
(45) Date of Patent: Dec. 10, 2019

(54) MODULAR INTERBODY FUSION DEVICE

(71) Applicant: SPINE WAVE, INC., Shelton, CT (US)

(72) Inventors: Edward Charles Skolnick, Norwalk, CT (US); Christopher P. Carson, Seymour, CT (US)

(73) Assignee: SPINE WAVE, INC., Shelton, CT (US)

( * ) Notice: Subject to any disclaimer, the term of this patent is extended or adjusted under 35 U.S.C. 154(b) by 336 days.

(21) Appl. No.: 15/293,391

(22) Filed: Oct. 14, 2016

(65) Prior Publication Data
US 2018/0104067 A1    Apr. 19, 2018

(51) Int. Cl.
 *A61F 2/44* (2006.01)
 *A61F 2/46* (2006.01)
 *A61F 2/30* (2006.01)

(52) U.S. Cl.
 CPC .......... *A61F 2/447* (2013.01); *A61F 2/30744* (2013.01); *A61F 2/4455* (2013.01); *A61F 2/4611* (2013.01); *A61F 2002/30187* (2013.01); *A61F 2002/30383* (2013.01); *A61F 2002/30481* (2013.01); *A61F 2002/30593* (2013.01); *A61F 2002/30604* (2013.01); *A61F 2002/30904* (2013.01); *A61F 2002/4475* (2013.01); *A61F 2310/00017* (2013.01); *A61F 2310/00023* (2013.01); *A61F 2310/00029* (2013.01); *A61F 2310/00131* (2013.01); *A61F 2310/00161* (2013.01); *A61F 2310/00167* (2013.01); *A61F 2310/00203* (2013.01); *A61F 2310/00239* (2013.01)

(58) Field of Classification Search
 CPC .......................... A61F 2/4611; A61F 2/44–447
 See application file for complete search history.

(56) References Cited

U.S. PATENT DOCUMENTS

| | | |
|---|---|---|
| 3,574,381 A | 4/1971 | Ocheltree |
| 5,397,364 A | 3/1995 | Kozak et al. |
| 5,782,830 A | 7/1998 | Farris |
| 6,235,059 B1 | 5/2001 | Benezech et al. |
| 6,447,546 B1 | 9/2002 | Bramlet et al. |
| 6,468,311 B2 | 10/2002 | Boyd et al. |

(Continued)

FOREIGN PATENT DOCUMENTS

FR     2827156 A1    1/2003

*Primary Examiner* — Nicholas J Plionis
(74) *Attorney, Agent, or Firm* — Hoffman & Baron, LLP

(57) ABSTRACT

A modular anterior lumbar interbody fusion device comprises a monolithic interbody fusion cage and a modular plate resiliently attached thereto. The cage includes an open architecture with top and bottom cross members and a pair of opposing arms projecting from respective side structures of the cage to define a pocket at the cage anterior end. The modular plate is received in the pocket and attached to the cage by resilient latches. The plate lies fully within the profile of the cage with the resilient latches lying fully within the thickness of the plate. The plate provides a structure to close the anterior portion of the modular cage after introduction of bone graft material while allowing for use with integrated fixation. Attachment features between the monolithic cage and modular plate are universal allowing for selection of various modular device configurations with minimal components.

19 Claims, 7 Drawing Sheets

(56) References Cited

U.S. PATENT DOCUMENTS

| | | |
|---|---|---|
| 6,558,388 B1 | 5/2003 | Bartsch et al. |
| 7,232,464 B2 | 6/2007 | Mathieu |
| 7,235,082 B2 | 6/2007 | Bartish et al. |
| 7,594,931 B2 | 9/2009 | Louis et al. |
| 7,674,297 B2 | 3/2010 | Falahee |
| 7,846,207 B2 | 12/2010 | Lechmann et al. |
| 8,062,303 B2 | 11/2011 | Berry et al. |
| 8,147,556 B2 | 4/2012 | Louis et al. |
| 8,268,000 B2 | 9/2012 | Waugh et al. |
| 8,273,127 B2 | 9/2012 | Jones et al. |
| 8,282,682 B2 | 10/2012 | Kirschman |
| 8,328,872 B2 | 12/2012 | Duffield et al. |
| 8,454,700 B2 | 6/2013 | Lemoine et al. |
| 8,460,388 B2 | 6/2013 | Kirwan et al. |
| 8,709,083 B2 | 4/2014 | Duffield et al. |
| 8,728,165 B2 | 5/2014 | Parry et al. |
| 8,864,830 B2 | 10/2014 | Malandain |
| 9,033,993 B2 | 5/2015 | Bae et al. |
| 9,078,765 B2 | 7/2015 | Louis et al. |
| 9,101,489 B2 | 8/2015 | Protopsaltis et al. |
| 9,155,631 B2 | 10/2015 | Seifert et al. |
| 9,161,841 B2 | 10/2015 | Kana et al. |
| 9,241,809 B2 | 1/2016 | McDonough et al. |
| 9,358,134 B2 | 6/2016 | Malandain |
| 9,480,577 B2 | 11/2016 | Despiau et al. |
| 2003/0233145 A1* | 12/2003 | Landry ............... A61B 17/025 623/17.11 |
| 2006/0129238 A1* | 6/2006 | Paltzer ............... A61F 2/447 623/17.11 |
| 2007/0250167 A1 | 10/2007 | Bray et al. |
| 2008/0140207 A1* | 6/2008 | Olmos ............... A61F 2/4611 623/17.16 |
| 2008/0208342 A1* | 8/2008 | Hanson ............... A61F 2/447 623/17.16 |
| 2008/0249569 A1 | 10/2008 | Waugh et al. |
| 2008/0281425 A1 | 11/2008 | Thalgott |
| 2010/0145459 A1 | 6/2010 | McDonough et al. |
| 2010/0298941 A1* | 11/2010 | Hes ............... A61F 2/4425 623/17.16 |
| 2012/0197317 A1* | 8/2012 | Lezama ............... A61F 2/4611 606/86 A |
| 2012/0197401 A1 | 8/2012 | Duncan et al. |
| 2012/0253406 A1 | 10/2012 | Bae et al. |
| 2012/0277872 A1 | 11/2012 | Kana et al. |
| 2012/0277873 A1 | 11/2012 | Kana et al. |
| 2014/0277477 A1* | 9/2014 | Malandain ............... A61F 2/442 623/17.16 |
| 2014/0277745 A1 | 9/2014 | Kirschman |
| 2015/0100125 A1* | 4/2015 | Protopsaltis ............... A61F 2/447 623/17.15 |
| 2015/0202051 A1 | 7/2015 | Tanaka et al. |
| 2015/0305883 A1 | 10/2015 | Garber et al. |
| 2016/0015523 A1 | 1/2016 | Lewis et al. |
| 2016/0151166 A1 | 6/2016 | Morris et al. |
| 2016/0324657 A1 | 11/2016 | Walkenhorst et al. |
| 2016/0338849 A1* | 11/2016 | Ashleigh ............... A61F 2/4455 |
| 2016/0374831 A1* | 12/2016 | Duffield ............... A61F 2/4611 623/17.16 |

* cited by examiner

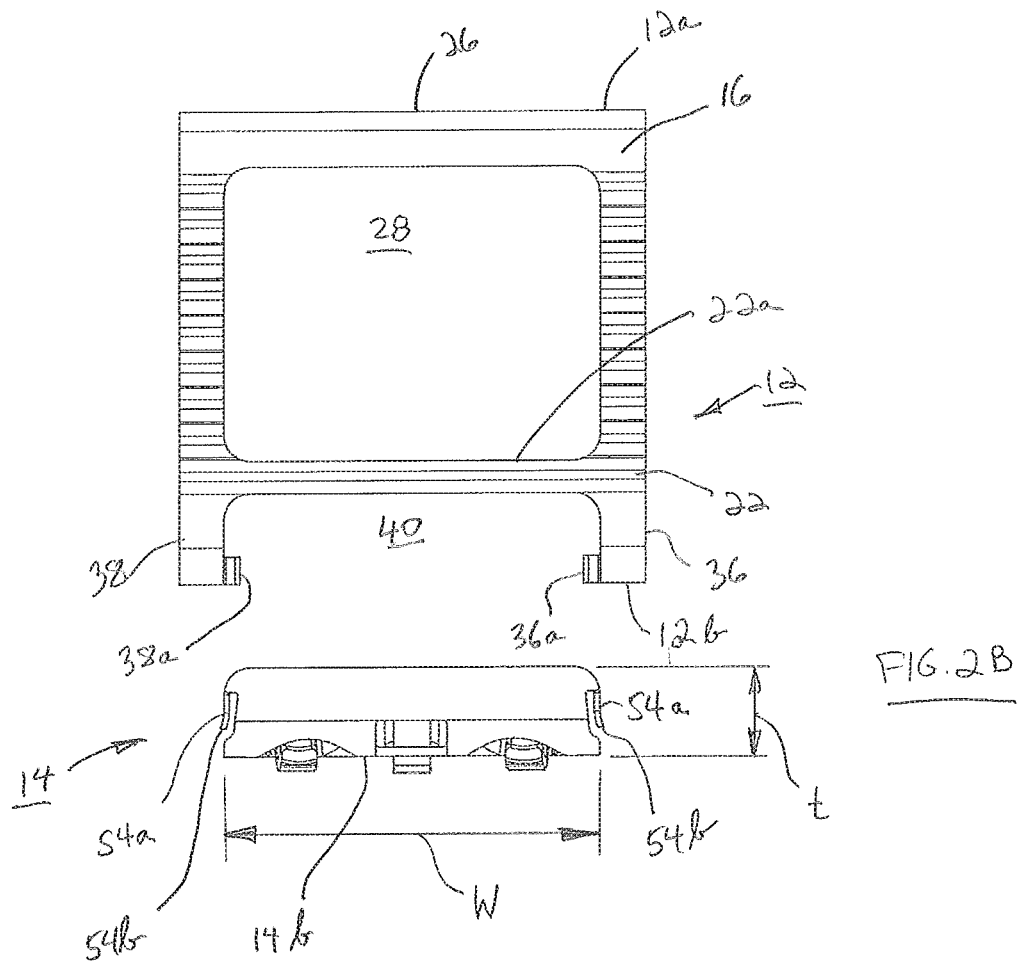
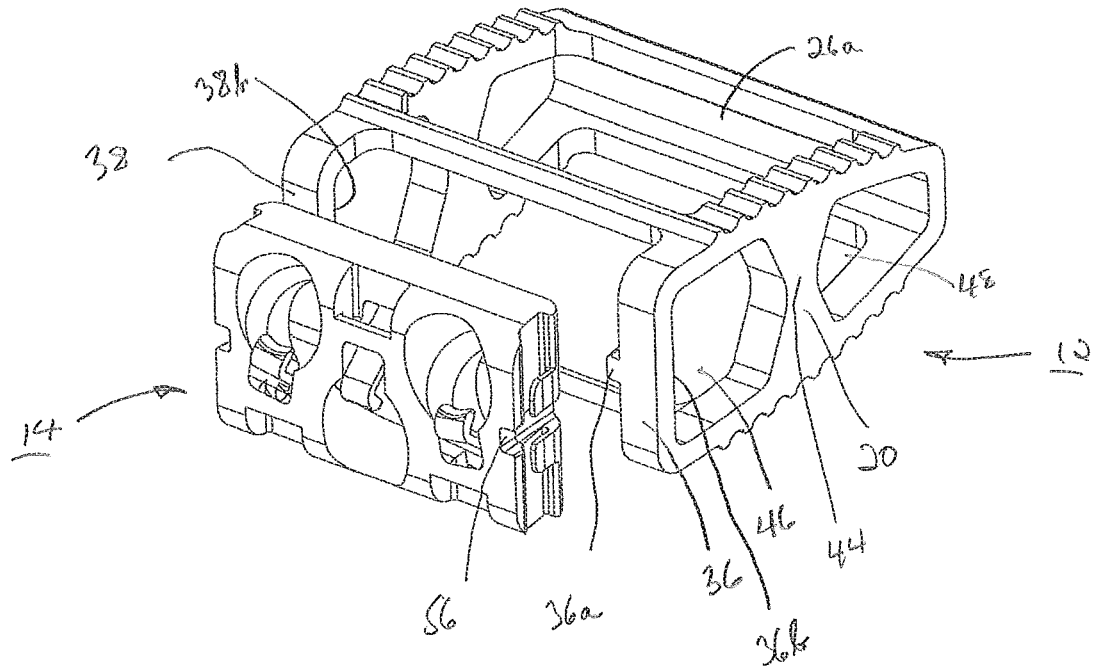

US 10,500,063 B2

MODULAR INTERBODY FUSION DEVICE

FIELD OF THE INVENTION

The subject invention relates generally to the field of interbody fusion devices and more particularly to modular anterior lumbar interbody fusion devices and related insertion instruments.

BACKGROUND OF THE INVENTION

Spinal implants such as spinal interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone graft or bone substitute material is placed substantially in and/or adjacent the device in order to promote fusion between two adjacent vertebrae.

There are various approaches that a surgeon may take to perform spinal fusion. Such approaches include a posterior approach, which is accessed from the back of the spine, or an anterior approach, which is accessed from the front. Other approaches which may be used include a posterolateral approach, an anterior lateral approach, and a lateral approach which is accessed from the side of the patient. The particular approach selected is primarily determined by the type of treatment to be administered by the surgeon. For patients that require treatment for conditions including degenerative disc disease, spinal instability or deformity, anterior lumbar interbody fusion (ALIF) has been found to be effective. The ALIF procedure and associated devices have certain advantages over other procedures. The first is that there is typically less disruption to surrounding musculature and nerves. Once access is achieved, there is a relatively open space to work in. This allows for more efficient removal of disc material thereby providing a larger potential fusion bed. The ALIF procedure also allows for a larger implant both in footprint and height, which creates better height and lordosis restoration as well as greater spinal stability.

Anterior lumbar interbody fusion requires an incision through the patient's abdomen and retraction of the surrounding muscles and abdominal contents to the side. After the affected disc is removed a structural ALIF device or implant is inserted which may be packed before, during or after insertion with a suitable bone graft material. Having a modular implant system has been found to be advantageous for an ALIF procedure as well as other procedures. This is desirable because it provides the surgeon the means to optimize fit and function of the implant system based on surgical preference. Specifically, having various implant configurations allows for complete functional modularity during a given procedure including: full construct (stand-alone indication with integrated fixation), cage-plate (supplemental fixation indication), and cage alone (supplemental fixation indication) configurations. Furthermore, it allows for maximizing visualization within the disc space, optimizing grafting volume/potential through post-pack, and promoting greater fusion by allowing for more efficient endplate preparation. Finally, it provides a baseline system from which other useful implant configurations and/or components can be added.

Known modular spinal implant systems are disclosed, for example, in U.S. Patent Publication 2014/0277456, entitled "Spinal Implant and Assembly", published Sep. 18, 2014 and filed by David Louis Kirschman, and in U.S. Patent Publication 2012/0197401, entitled "Interbody Spinal Implants with Modular Add-on Devices", published Aug. 2, 2012 and filed by James Duncan et al. While filling certain surgical needs, there is still interest in improved modular interbody devices fusion devices.

SUMMARY OF THE INVENTION

It is an object of the invention to provide an improved modular interbody fusion device. A further object is to provide an inserter for releasable attachment to the modular interbody fusion device for insertion of the device into an intradiscal space between opposing vertebral bodies of a spine.

DESCRIPTION OF THE FIGURES

FIG. 2A is a top exploded perspective view of the device of FIG. 1A, showing the monolithic cage and modular plate before attachment.

FIG. 2B is a top exploded view of the monolithic cage and modular plate of FIG. 2A.

DESCRIPTION OF THE EMBODIMENTS

Figure 1B:
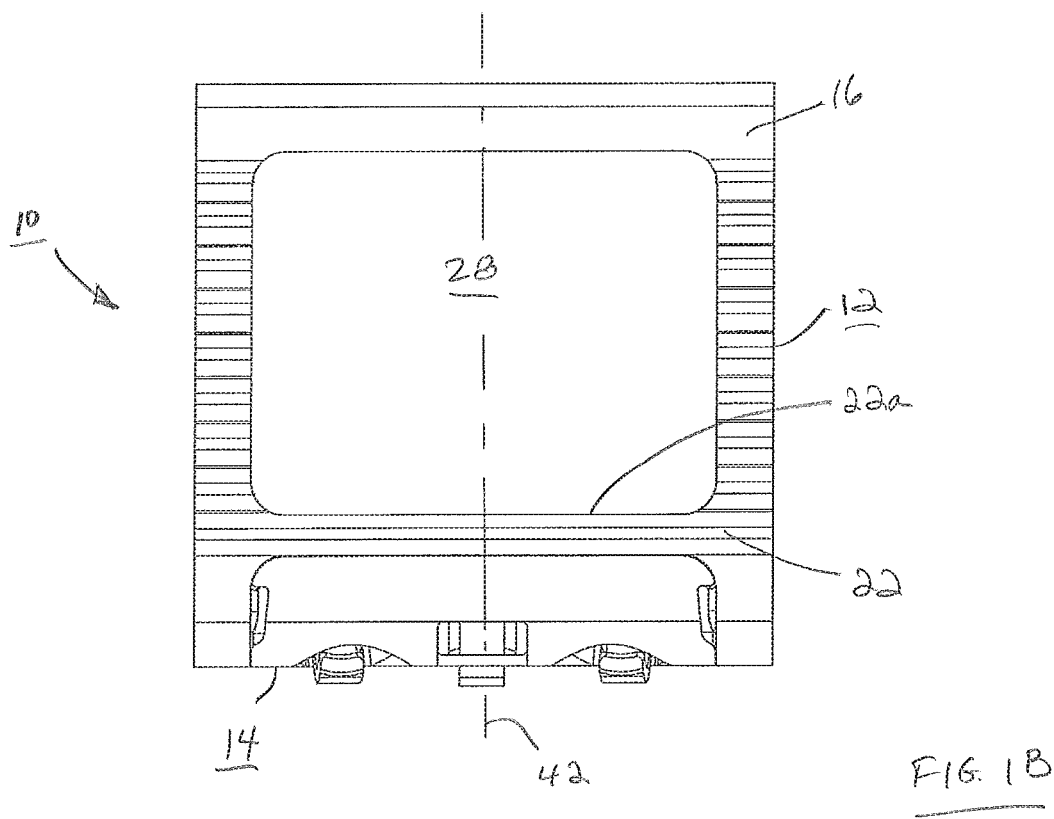
FIG. 1B is top plan view of the device of FIG. 1A.

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring to FIGS. 1A, 1B and 2A, 2B, there is shown a modular interbody fusion device 10 for insertion into the intradiscal space between opposing vertebrae comprising a monolithic cage 12 and an attachable modular plate 14. In particular, device 10 as described herein is suitable as a spinal fusion implant configured to contact endplates of opposing vertebral bodies in a spine defining a volume between vertebrae in the intradiscal space after a natural disc has been removed in preparation for the implantation of the device. In the embodiment shown, modular interbody fusion device 10 is configured and sized for particular application in the lumbar section of the spine with insertion from the anterior approach. Other applications and insertion directions, however, are also contemplated, as will be described.

Figures 3, 4, 5:
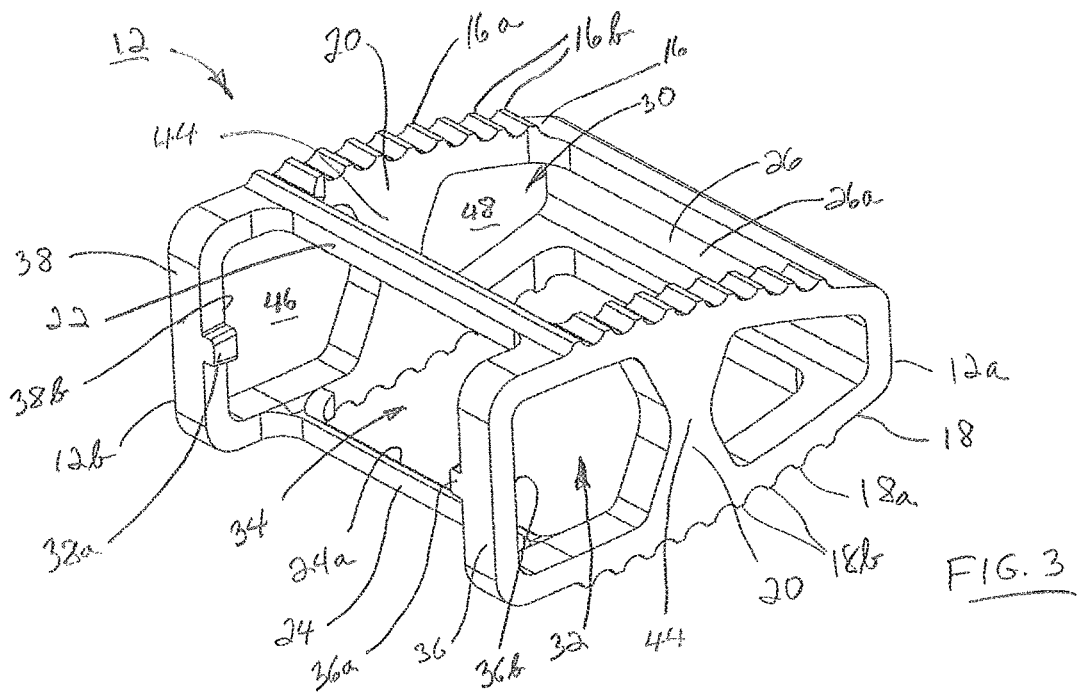
FIG. 3 is a top perspective view of the monolithic cage of the device of FIG. 1A.
FIG. 4 is a top perspective view of the modular plate of the device of FIG. 1A.
FIG. 5 is a cross-sectional view of the modular plate as seen along viewing lines V-V of FIG. 4.
Figure 6:
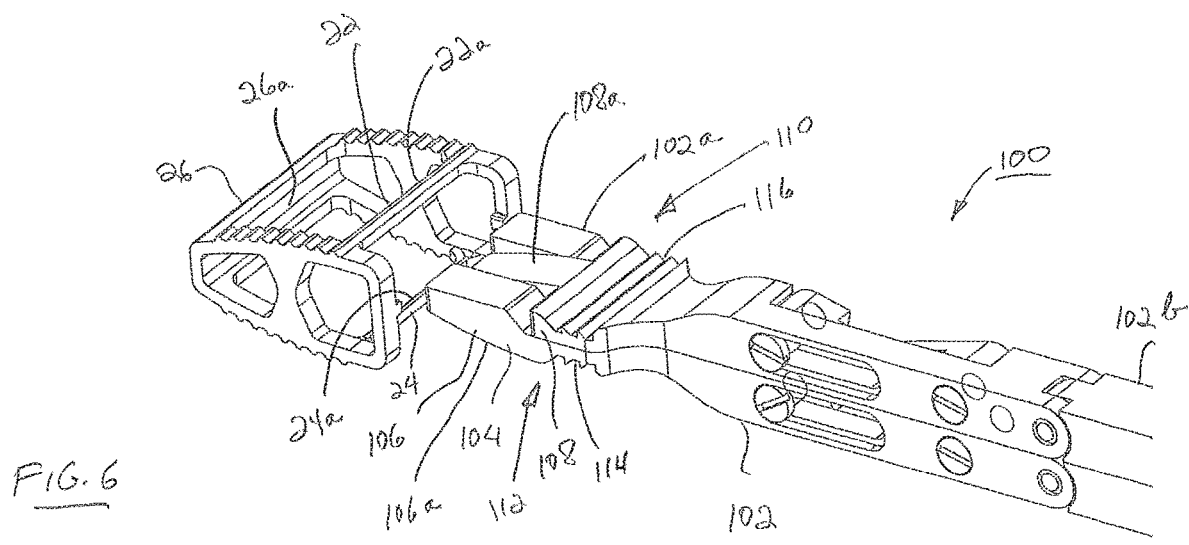
FIG. 6 is a top exploded perspective view of the monolithic cage of FIG. 3 and an inserter of the present invention prior to attachment of the inserter to the cage.

Referring also to FIG. 3, details of monolithic cage 12 may be more fully understood. Cage 12 is a monolithic body having a distal end 12a and a proximal end 12b, an upper bone contact structure 16, a lower bone contact structure 18 and a pair of spaced apart side structures 20 joining upper bone contact structure 16 and lower bone contact structure 18. Cage 12 includes an outer top surface 16a supported by the underlying upper bone contact structure 16, and an outer bottom surface 18a supported by the underlying lower bone contact structure 18. Top surface 16a and bottom surface 18a are preferably contoured as curved, convex surfaces so as to match the anatomic convexity and size of the cartilaginous endplates of the respective mating vertebral body surfaces. This anatomical fit ensures proper bony engagement to provide biomechanical support of the bony surfaces to resist device subsidence during expansion. Upper bone contact structure 16 and lower bone contact structure 18 include thereon a number of serrations 16b and 18b serving a bone anchoring function, the apices of serrations 16b, 18b respectively defining top surface 16a and bottom surface 18a of cage 12. These functional anchors may assist in holding the device 10 in position during implantation or may hold the device 10 in position after implantation. Other forms of functional bone anchoring components, e.g., fins, spikes, hooks, etc., may be substituted as desired. It should also be understood that top and bottom surfaces 16a, 18a may in certain situations be formed to have a contour other than convex, such as being linear. Furthermore, one surface, such as top surface 16a may be curved while bottom surface 18a may be linear.

In the particular application shown, device 10 is a modular anterior lumbar interbody fusion (ALIF) device wherein distal end 12a is the posterior end and proximal end 12b is the anterior end. In such arrangement, monolithic cage 12 is of fixed dimension, and the height of posterior distal end 12a is less than the height of anterior proximal end 12b, with upper and lower bone contact structures 16, 18 inclining toward each other distally to thereby define a wedge-shaped lordotic configuration for anterior placement. It should be appreciated, however, that only one of upper bone contact structure 16 or lower bone contact structure 18 may be angled toward the other. In an example where cage 12 is symmetrical about its longitudinal centerline, each of upper and lower bone contact structures 16, 18 is angled approximately the same amount from the centerline of device 10. As such, where cage 12 is provided to have a 15 degree lordotic angle, upper bone contact structure 16 is 7.5 degrees from the centerline and the lower bone contact structure 18 is 7.5 degrees front the centerline as well. The included angle between upper and lower bone contact structures 16 and 18 is 15 degrees, in this example. It should be understood that in some instances monolithic cage 12 may be expandable and also sized and configured to conform to other interbody fusion procedures.

Figure 1A:
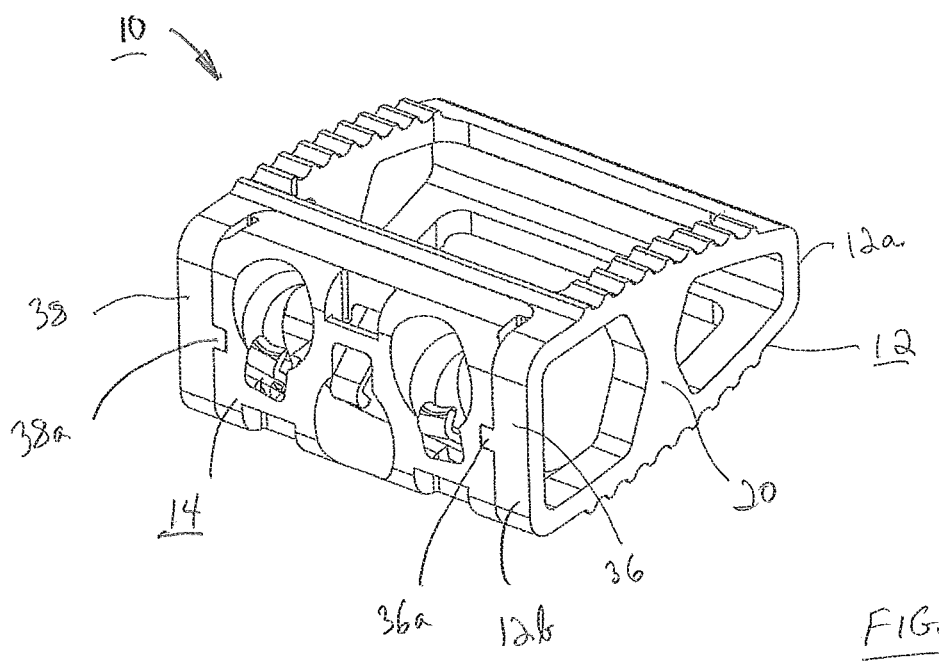
FIG. 1A is a top perspective view of a modular anterior lumbar interbody fusion device in accordance with an embodiment of the present invention.

Referring still to FIGS. 1A, 2A and 3, further details of cage 12 are described. Opposing spaced apart side structures 20 of cage 12 are interconnected to each other adjacent proximal end 12b by a laterally extending top cross member 22 and a laterally extending bottom cross member 24. The distal-facing surfaces 22a (FIGS. 1B and 2B) and 24a (FIG. 3) of top cross member 22 and bottom cross member 24 provide respective instrument engagement surfaces for releasable connection with an insert or instrument, and will be described. Opposing spaced apart side structures 20 of cage 12 are interconnected to each other adjacent distal end 12a by a laterally extending closed posterior end wall 26. The upper and lower bone contact structures 16, 18, side structures 20 and rear end wall 26 define a hollow interior 28 of cage 12.

Upper and lower bone contact structures 16, 18 include upper and lower openings 30 and 32 respectively therethrough allowing bone graft or other osteogenic materials to flow into the hollow interior 28 of the cage 12 and to pass through and contact adjacent vertebral body endplates thereby aiding in the fusion of the device 10 thereto. The top cross member 22, posterior end wall 26 and opposing side structures 20 define upper opening 30 through top surface 16a, while the bottom cross member 24, posterior end wall 26 and side structures 20 define lower opening 32 through bottom surface 18a. A proximal opening 34 is defined between top and bottom cross members 22, 24 and side structures 20. Upper opening 30, lower opening 32 and proximal opening 34 all communicate with hollow interior 28.

Proximal end 12b of cage 12 is defined by a pair of spaced opposing arms 36 and 38 projecting proximally from side structures 20, with arms 36 and 38 interconnecting upper and lower bone contact structures 16, 18. Arms 36 and 38 together with top and bottom cross members 22, 24 define a pocket 40 (FIG. 2B) for resilient receipt of modular plate 14 as will be described. Pocket 40 communicates with proximal opening 34. Each arm 36, 38 includes thereon a key 36a, 38a extending into pocket 40 and projecting laterally toward each other. Keys 36a and 38a are disposed approximately midway between upper and lower bone contact surfaces 16, 18 at the proximal end 12b. Arms 36, 38 each define a generally blunt trailing end while the distal end 12a is defined by end wall 26 which similarly includes a generally blunt leading end. The generally blunt ends allow the upper and lower bone contact structures 16, 18 to have a length along and generally parallel to axis 42 optimized for maximum contact with endplates of opposing vertebral bodies.

Side structures 20 each comprise a generally centrally located load bearing column 44 and a pair of windows 46 and 48 respectively extending therethrough and communicating with the hollow interior 28. Communicating with respective windows 46 are latch engagement surfaces 36b and 38b on the distal surfaces of arms 36 and 38 for engagement with a resilient latch on modular plate 14, as will be described Referring now to FIGS. 4-5 as well as FIG. 2B, details of modular plate 14 are described. Plate 14 is generally rectangular in configuration having a height, H (as illustrated in FIG. 5), a width, W and a thickness, t, as shown in FIG. 2B. Height, H, width, W and thickness, t, are all sized and configured such that modular plate 14 fits fully within pocket 40 of cage 12, as will be described, without adding to the profile of cage 12. Plate 14 in one arrangement has three openings 50 extending therethrough for receipt and retention of fixation elements, such as bone screws, described hereinbelow. Each opening 50 is oriented with its axis 50a (FIG. 5) lying obliquely with respect the height, H of plate 14. In the shown arrangement, the axes 50a of the two outside holes 50 are generally parallel to each other, with each of these holes 50 being oriented to receive a respective fixation element for attachment to an endplate of an inferior vertebral body. The axis 50a of middle hole 50 in the shown arrangement is transverse to the axes 50a of the two outside holes, with middle hole 50 being oriented to receive a fixation element for attachment to an endplate of a superior vertebral body. It should be appreciated that a different number of holes with other axis orientations may also be contemplated.

Associated with each hole 50 is a screw retention clip 52 for retaining a fixation element in place without backing out after implantation. Clip 52 comprises a cantilevered arm 52a that is joined to plate 14 within hole 50 at one end and that terminates at its free end in a flange 52b that extends transversely relative to axis 50a. As the head of a fixation element such as a bone screw extends into hole 50, the bone screw head will temporarily displace clip arm 52a until the head passes flange 52b at which time arm 52a will spring back with flange 52b overlying the head of the bone screw, as will be described. In the described arrangement, modular plate 14 and clip 52 are integrally formed as a unitary piece formed of the same material. However, it should be understood that clip 52 may be formed separately out of the same or different material as plate 14 and attached to plate 14 by any suitable technique.

Disposed on each of the side surfaces 14a of plate 14 is a resilient latch 54 for resiliently attaching plate 14 to cage 12. In the arrangement shown latch 54 comprises a pair of cantilevered latch elements 54a spaced by a keyway 56 therebetween. Each latch element is attached to a respective side surface 14a of plate 14 at one end with its free end 54b extending toward the anterior surface 14b of plate 14, as shown in FIG. 2B. As further seen in FIG. 2B, resilient latch 54 is configured and sized to lie fully within the confines of the thickness, t of modular plate 14. As seen in FIG. 4, resilient latch 54 is also configured and sized to lie fully within the confines of the height, H of modular plate 14. Each keyway 56 is sized and dimensioned to respectively receive keys 36a, 38a in a manner to guide plate 14 into pocket 40 during attachment to cage 12. Like keys 36a, 38a, keyways 56 are disposed approximately midway between the top and bottom surfaces 14c and 14d of plate 14. The midway disposition of the keys 36a, 38a and keyways 56 allow for a universal connection feature between a single modular plate 14 and different size cages 12, as will be described. Upon receipt of plate 14 into pocket 40 of cage 10 as guided by keys 36a, 38a and keyways 56 to form interbody fusion device 10, the free cantilevered ends 54b of latch elements 54 resiliently engage latch engagement surfaces 36b and 38b on the distal surfaces of arms 36 and 38 to attach plate 14 to cage 12. While latch engagement surfaces 36b and 38b in the described arrangement as being disposed on distal surfaces of arms 36 and 38, it should be appreciated that in other arrangements latch engagement surfaces may be provided on the distal surfaces of cross members 22 and 24. In such other arrangements, a resilient latch is 54 may be provided on top surfaces 14c, 14d respectively for complementary engagement with such latch engagement surfaces, with such latches being disposed within the confines of plate thickness, t.

Suitable biocompatible metallic materials for cage 12 and modular plate 14 include pure titanium, tantalum, cobalt-chromium alloys, titanium alloys (e.g., nickel titanium alloys and tungsten titanium alloys), and stainless steel alloys. Suitable polymeric materials for cage 12 and modular plate 14 include members of the polyaryletherketone (PAEK) family, e.g., polyetheretherketone (PEEK), carbon-reinforced PEEK, polyetherketoneketone (PEKK); polysulfone; polyetherimide; polyimide; ultra-high molecular weight polyethylene (UHMWPE); or cross-linked UHMWPE. Ceramic materials such as aluminum oxide or alumina, zirconium oxide or zirconia, compact of particulate diamond, or pyrolytic carbon may be included in such polymers.

Figure 9A:
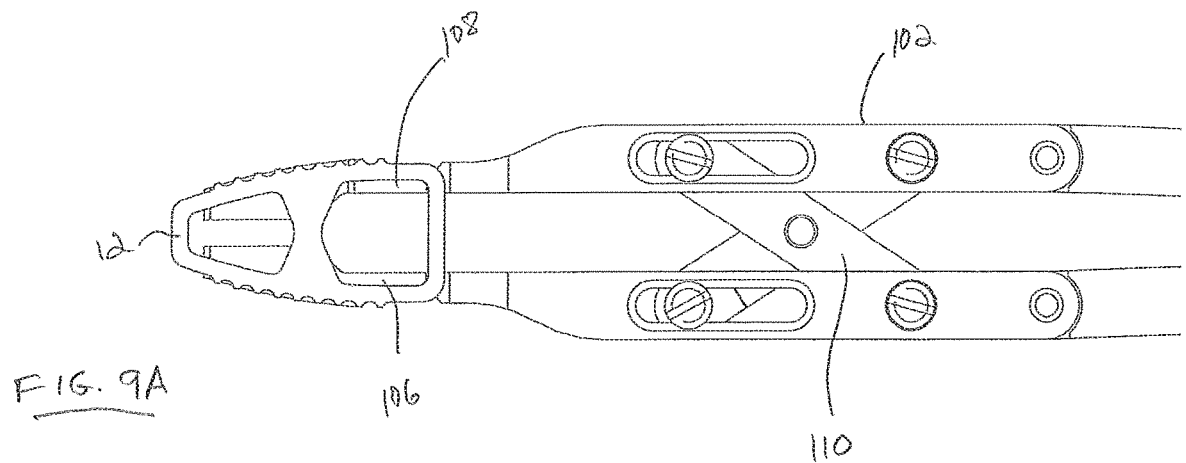
FIG. 9A is a side elevation view of the monolithic cage and inserter of FIG. 8 with the expandable tip portion of the inserter expanded and attached to the monolithic cage after expansion.
Figure 8:
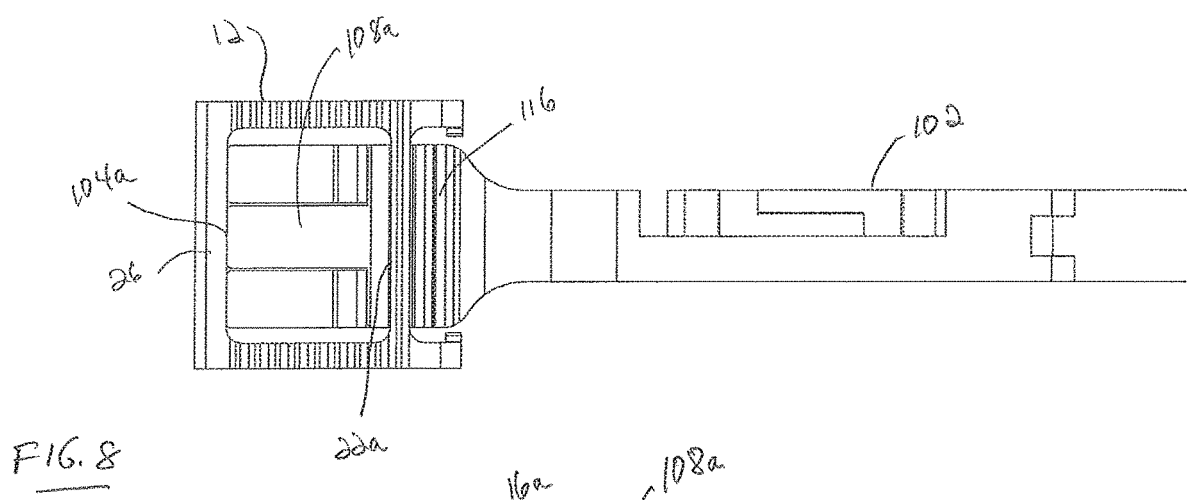
FIG. 8 is a top plan view of the monolithic cage and inserter of FIG. 6 with an expandable tip portion of the inserter inserted into the monolithic cage prior to expansion.

Turning now to FIGS. 6-8, 9A and 9B, the details of an instrument for inserting cage 12 into the intradiscal space between the endplates of opposing vertebral bodies are described. Inserter 100 comprises an elongate cage holder 102 having a distal end 102a and a proximal end 102b. Proximal end 102b is of size and configuration for grasping by a surgeon and of extent to extend outwardly of the surgical site of a patient. Distal end 102a terminates in an expandable tip portion 104 specifically configured for receipt through proximal opening 34 and into interior 28 of cage 12. Expandable tip portion 104 includes a pair of plates, namely lower plate 106 and upper plate 108 that are movably separable in a direction transverse to the elongate direction of holder 102 by a linkage mechanism 110, as illustrated in FIG. 9A. Mechanism 110 may be actuated manually by a pliers type handle at the proximal end 102b (not shown) or any other suitable actuation technique. Inserter 100 is formed of stainless steel although other suitable materials may be used.

Figure 7:
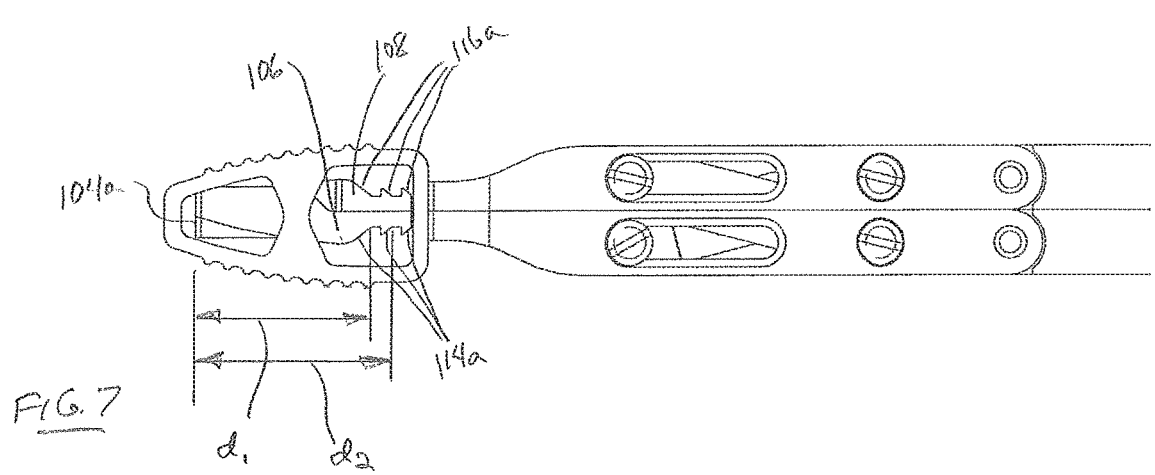
FIG. 7 is a side exploded elevation view of the exploded monolithic cage and inserter of FIG. 6.

In accordance with a particular arrangement, each of the movable plates 106 and 108 is provided with a connection surface 110 and 112, respectively, that is defined by a plurality of laterally extending, axially spaced grooves 114 and 116. Each groove 114, 116 is spaced from the distal end 104a of the expandable distal top portion 104 by a different dimension, e.g., $d_1$ and $d_2$, as shown in FIG. 7. Each groove 114, 116 has an inclined surface 114a, 116a adjacent thereto, such inclined surfaces 114a, 116a being oriented to face in the proximal direction. Upon insertion of the expandable distal tip portion 104 into the interior 28 of cage 12, the distal end 104a is configured to engage an interior surface 26a of posterior end wall 26. Upon expansion of expandable tip portion 104 by separation of plates 106, 108, one of the grooves 114 on lower plate 106 is configured to engage engagement surface 24a on bottom cross member 24 while one of the grooves 116 upper plate member 108 is configured to engage engagement surface 22a of top cross member 22. As plates 106, 108 further separate, engagement of inclined surfaces 114a, 116a with engagement surfaces 24a, 22a will cause distal end 104a to move forcibly against interior surface 26a of posterior end wall 26 to thereby make a tight connection between expandable tip portion 104 and cage 12.

The function of the formation of the multiple grooves 114, 116 on cage holder 102 is to allow the use of a single inserter 100 with a plurality of different cages 12, each having at least different lengths. The dimension $d_1$, $d_2$, etc. between the distal end 104a of holder 102 and each groove 114, 116 is formed to substantially match the respective different distance that each cage 12 is spaced between the posterior interior surface 26a of posterior end wall 26 and the instrument engagement surfaces 22a and 24a. As such, where three grooves 114, 116 are provided on holder 102, three differently size cages 12 may be provided in a kit of parts to be selected by the surgeon in accordance with surgical and anatomical conditions. It should be appreciated, however, that more or less than three grooves 114, 116 may be provided with a commensurate number of differently sized cages 12.

Figure 9B:
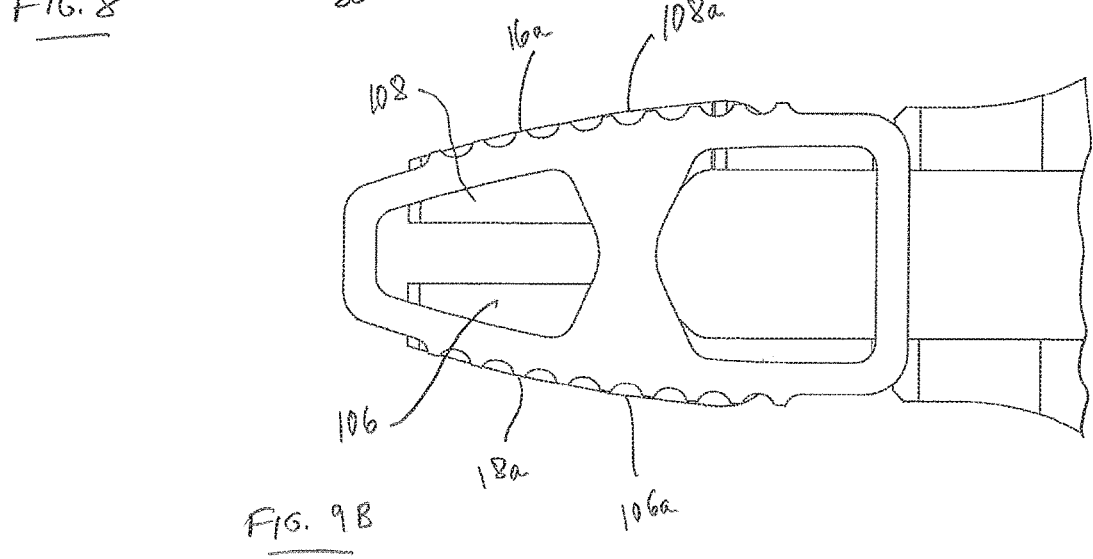
FIG. 9B is an enlarged view of the expandable tip portion of the inserter attached to the monolithic cage as shown in FIG. 9A.

Additionally, lower plate 106 and upper plate 108 are each configured to have an exterior surface that is formed to substantially match the outer contour of the top surface 16a and bottom surface 18a of cage 12. Where top surface 16a and bottom surface 18a are convex as described hereinabove, the exterior surfaces are formed to substantially match the radius of curvature of such convexities. As such, upper plate 108 includes a central convex exterior surface 108a while lower plate 106 has a pair of convex exterior surfaces 106a on each lateral side of upper exterior surface 108a, as shown in FIG. 9A. Upon expansion of distal tip portion 104, upper exterior surface 108a extends into upper opening 30 of cage 12 while lower exterior surfaces 106a extends into lower opening 32 of cage 12. Upon full expansion of expandable tip portion 104 and secure attachment to cage 12, exterior surfaces 106a, 108a lie no less than flush with respect to top surface 16a and bottom surface 18a along substantially the full axial length of exterior surfaces 106a, 108a, as shown in FIG. 9B. Accordingly, surface 106a may lie slightly exteriorly below bottom surface 18a, while exterior surface 108a may lie slightly exteriorly above top surface 16a.

A kit of parts including a plurality of cages 12 discussed above may be provided where the cages 12 are formed to include a variety of different lengths and differing widths or heights, or are selected to include differing lordotic angles between the distal and proximal ends 12a, 12b. Each of these kits may include a single inserter 100 for attachment to a selected cage 12 and introduction of the selected cage 12 into a chosen site in the intradiscal space between opposing vertebral bodies. Further, the kit of parts may include a single modular plate 14 that is configured to be received within the pocket 40 of any of the plurality of cages for attachment to such cage. In such kit, the pocket 40 of each of cages 12 is configured to be of approximately the same size and shape such that a modular plate 14 may be received therein for attachment to the selected cages 12, as will be described.

Having described the structure and function of the modular components of device 10 herein, the method of using device 10 in an anterior lumbar interbody fusion is now described. An incision is made through the patient's abdomen and the surrounding muscles and abdominal contents are retracted to the side to form an open surgical access corridor. The affected disc is removed to provide a proper space between opposing vertebral bodies. The surgeon may determine the appropriate size of device 10 for insertion by using a suitable trailing device. Once the appropriate size is determined, a desired cage 12 is selected from the kit and suitably attached to cage holder 102 of inserter 100. Attachment is effected by introducing expandable tip portion 104 through proximal opening 34 of the selected cage 12 and into hollow interior 28 until distal end 104a of holder 102 contacts interior surface 26a of posterior end wall 26.

Figure 10:
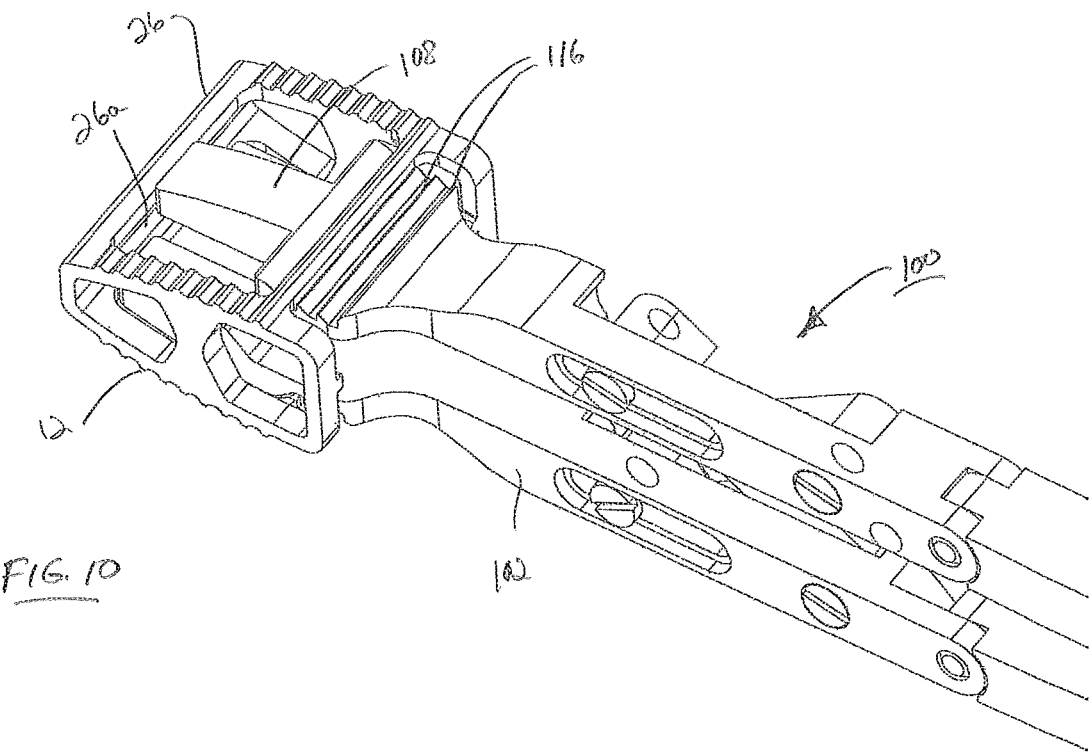
FIGS. 10 and 11 are perspective top views showing the expandable tip portion of the inserter attached to the monolithic cage after expansion.
Figure 11:
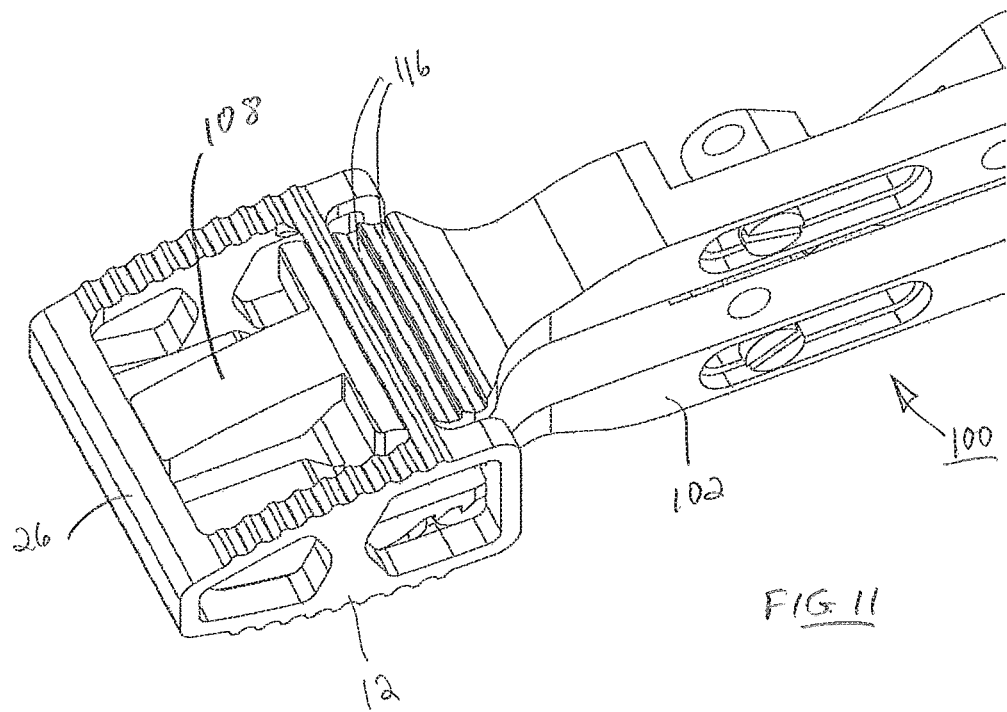

Expandable tip potion 104 is expanded by movably separating lower plate 106 and upper plate 108 away from each other by suitable actuation of inserter linkage mechanism 110. Upon expansion of lower and upper plates 106, 108, cross members 22 and 24 will engage one of the grooves 114, 116 as described above until tight connection between selected cage 12 and holder is achieved. Proper attachment of cage 12 with inserter 100 is shown in FIGS. 10 and 11, with cage 12 in position for insertion.

Cage 10 is then inserted into the disc space by inserter 100 through manipulation by the surgeon. As a result of lower exterior surface 106a and upper exterior surface 108a lying no less than flush with the contours of the respective bottom surface 18a and 16a as depicted in FIG. 9B, the surfaces of the endplates of opposing vertebral bodies adjacent the intradiscal space are protected from undue abrasion during insertion of cage 10. Upon appropriate positioning of cage 10 in the intradiscal space, inserter 100 is removed by suitably contracting expandable tip portion 104 by moving lower plate 106 and upper plate 108 toward each other and withdrawing cage holder 102 from inserted cage 12. The open architecture of cage 12 allows for proper preparation of the opposing vertebral body endplates whereby disc preparation tools may be introduced through proximal opening 34 of cage 12 and then through upper opening 30 and lower opening 32 for direct access to the vertebral body endplates. The generally blunt proximal and distal ends of cage arms 36, 38 and of cage distal end 12a allow for optimization of implant length for maximum contact area between cage 12 and the opposing vertebral body endplates. The compression on cage 12 provided by the ligaments surrounding vertebral bodies on the serrations 16b and 18b will serve to anchor the cage 12 in position.

After implantation, all or a portion of the interior 28 of cage 12 as well as the disc space surrounding cage 12 may be filled in situ with a suitable bone graft material containing bone growth promoting substances. Osteogenic materials or therapeutic compositions may also be used, such materials and compositions being more fully described in commonly owned U.S. Pat. No. 8,641,769, entitled "A Plastically Deformable Inter-Osseous Device", issued to Hugues Malandain on Feb. 4, 2014, and incorporated in its entirety by reference herein.

Figure 12:
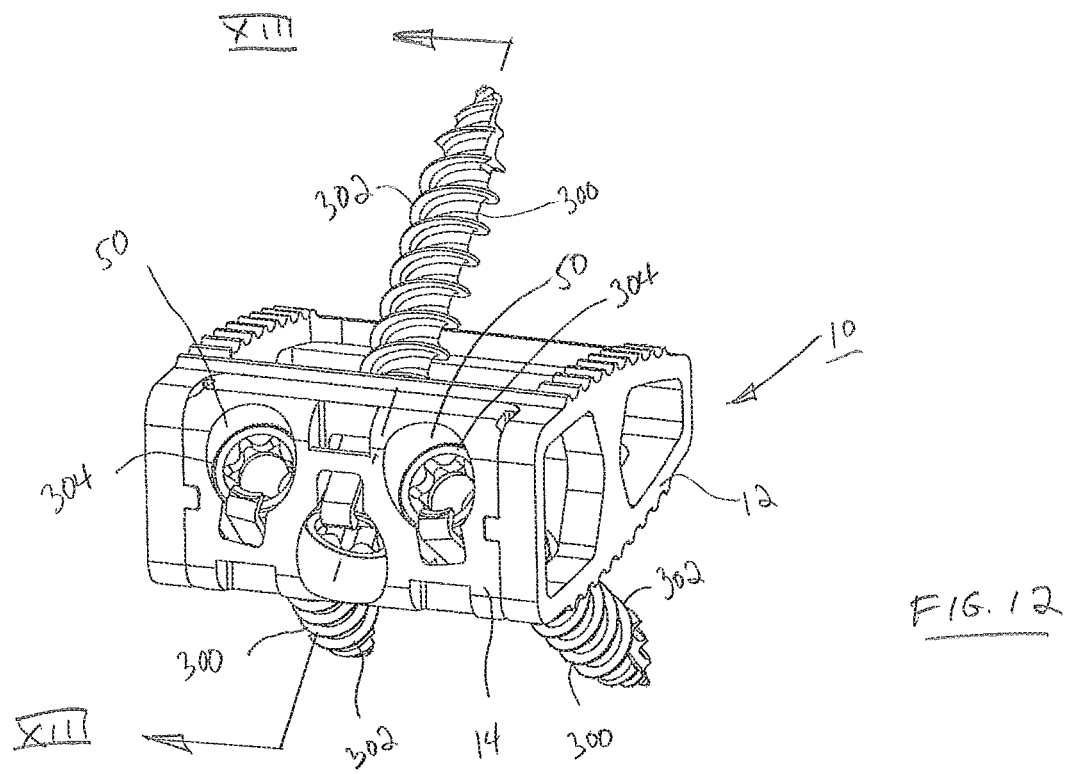
FIG. 12 is a top perspective view of the device of FIG. 1 with bone fixation screws extending therethrough.
Figure 13:
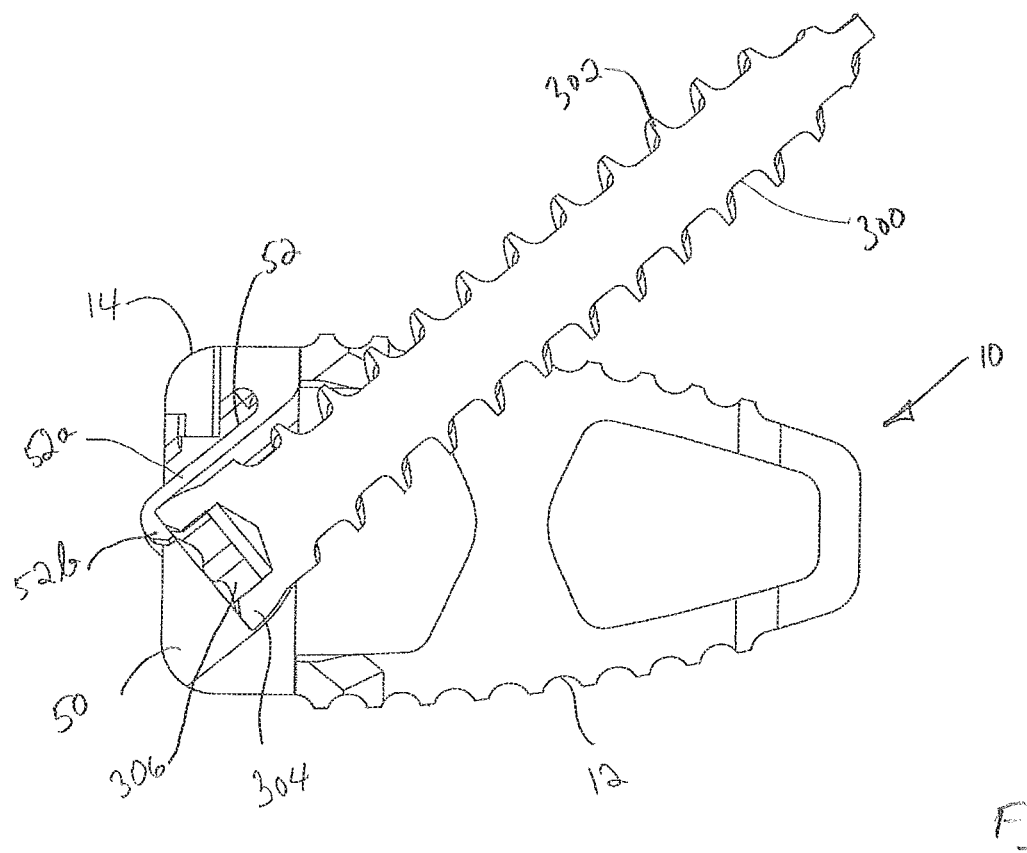
FIG. 13 is a cross-sectional view of the device and bone fixation screws as seen along viewing lines XIII-XIII of FIG. 12.

Following the placement of suitable bone graft material, modular plate 14 is resiliently attached in situ to the inserted cage 12 in a manner as described hereinabove with keys 36a, 38a on cage 12 guiding the attachment by complementary receipt into keyways 56 of modular plate 14. Resilient latching of latches 54 with latch engagement surfaces 36b and 38b on the distal surfaces of arms 36 and 38 completes the assembly of modular anterior lumbar interbody fusion device 10. Thus attached, modular plate 14 provides two functions. First, modular plate 14 serves as a barrier restricting backflow of bone graft material out from cage 12, thus contributing to the maintenance of compressive load between the graft material and the endplates of the opposing vertebral bodies. Second, modular plate 14 serves as a structure for the introduction of suitable fixation elements to stabilize the position of interbody fusion device 10 in the disc space. As shown in FIGS. 12 and 13, fixation element such as bone screws 300 may be introduced through plate openings 50 as described hereinabove. Each bone screw 300 includes a threaded elongate shaft 302 and an enlarged head 304 containing a suitable socket 306 for suitable attachment to a suitable driver. As each bone screw 300 passes through an opening 50 with threaded shafts entering respective vertebral body endplates, the head 304 of each bone screw 300 will temporarily displace clip arm 52a until the head 304 passes flange 52b, at which time arm 52a will spring back with flange 52b overlying the head 304 of bone screw 300. The disposition of flange 52b in overlying relation relative to head 304 will serve to restrict backout of bone screw 300 from interbody fusion device 10.

It should be appreciated that the modular anterior interbody fusion device 10 as described herein includes particular features that may be desirable to a surgeon. For example, the module cage 12 provides an accessible proximal opening that allows for clear visualization into the disc space after insertion while also providing a structure to prevent load induced subsidence by virtue of the anterior top and bottom cross members 22, 24 that span the width of cage 12. Such cross members 22, 24 also provide surfaces for engaging cage 12 during insertion/removal process. Further, modular plate 14 provides a structure to close the proximal portion of monolithic cage 12 after introduction of bone graft material while allowing for use with integrated fixation. In addition, since the attachment features between the modular cage 12 and modular plate 14 are universal throughout various configurations, flexibility for surgical use with minimal components is enhanced.

While the invention has been illustrated and described in detail in the drawings and foregoing description, the same should be considered as illustrative and not restrictive in character. For example, while one arrangement of a modular interbody fusion device 10 has been described herein as being particularly applicable for anterior lumbar fusion, it should be appreciated that modular interbody fusion device 10 may also be sized and configured for use in other sections of the spine, such as the cervical and thoracic spine, and may also be inserted in a posterior, posterolateral, anterior lateral or lateral approach. In addition, while cage 12 has been described in one arrangement as being monolithic, it should be understood that a cage formed of more than one part may also be use, particularly when used with the inserter 100 described herein. Accordingly, it should be appreciated that only the preferred embodiments have been presented and that all changes, modifications and further applications that come within the spirit of the invention are desired to be protected.

What is claimed is:

1. An apparatus for use in interbody fusion surgery, comprising in combination:
    an interbody fusion cage having a distal end, a proximal end having a proximal opening therethrough, a hollow interior communicating with said proximal opening, a top surface and a bottom surface, a pair of spaced apart side structures joining said top surface and said bottom surface, and an instrument engagement surface extending transversely to one of said top or bottom surfaces adjacent the proximal end of said cage and extending laterally between said side structures; and
    an inserter comprising an elongate cage holder, said cage holder comprising a proximal end and a distal end, the distal end extending through said proximal opening and within said hollow interior of said cage and terminating in an expandable tip portion comprising a connection surface in cooperative releasable engagement with said instrument engagement surface on said cage upon expansion of said tip portion, said connection surface including a plurality of laterally extending, axially spaced grooves, only one of said grooves being in selective engagement with said instrument engagement surface of said cage.

2. The apparatus of claim 1, wherein said expandable tip portion comprises a distal end, and wherein each of said grooves is spaced at a different axial dimension from said distal end.

3. The apparatus of claim 2, wherein said cage includes a distal end wall having an interior surface extending transversely to one of said top or bottom surfaces, said distal end of said expandable tip being configured to engage said interior surface upon insertion of said expandable tip into said hollow interior of said cage, and wherein said top surface includes a top cross member adjacent said proximal end of said cage and said bottom surface includes a bottom cross member adjacent said proximal end of said cage, said top cross member and said bottom cross member defining said proximal opening.

4. The apparatus of claim 3, wherein said instrument engagement surface includes a distal-facing surface on each of said top cross member and said bottom cross member axially spaced from said interior surface of said distal end wall at a predetermined distance.

5. The apparatus of claim 4, wherein said expandable tip portion comprises an upper plate and a lower plate movable during expansion in opposite directions transverse to the axial direction of said elongate cage holder, each of said upper plate and said lower plate comprising said plurality of grooves.

6. The apparatus of claim 5, wherein each of said grooves on said upper plate and said lower plate has adjacent thereto an inclined surface facing proximally, each of said inclined surfaces being configured to engage said distal-facing surface respectively on each of said top cross member and said bottom cross member when the distal end of said expandable tip engages said interior surface.

7. The apparatus of claim 6, wherein said top surface has an outer surface contour defining an opening therethrough in communication with said hollow interior and said bottom surface has an outer contour defining an opening therethrough in communication with said hollow interior.

8. The apparatus of claim 7, wherein said upper plate comprises an exterior surface having an outer contour and said lower plate comprises an exterior surface having an outer contour, the exterior surface of said upper plate and said lower plate projecting upon expansion into a respective opening through said top surface and said bottom surface of said cage and lying no less than flush with said respective top surface and said bottom surface of said cage.

9. The apparatus of claim 1, wherein said interbody fusion cage is sized and configured for anterior lumbar interbody fusion, wherein said distal end of said cage defines a posterior end and the proximal end defines an anterior end, and wherein the height at said anterior end is greater than the height at said posterior end.

10. The apparatus of claim 9, wherein said cage is monolithic and of fixed dimension.

11. An apparatus for use in interbody fusion surgery, comprising in combination:
    an interbody fusion cage having a distal end, a proximal end having a proximal opening therethrough, a hollow interior communicating with said proximal opening, a top surface and a bottom surface, and an instrument engagement surface adjacent the proximal end of said cage, said top surface having an outer surface contour defining an opening therethrough in communication with said hollow interior and said bottom surface having an outer contour defining an opening therethrough in communication with said hollow interior; and an inserter comprising an elongate cage holder, said cage holder comprising a proximal end and a distal end, the distal end extending through said proximal opening and within said hollow interior of said cage and terminating in an expandable tip portion comprising a connection surface in cooperative releasable engagement with said instrument engagement surface on said cage upon expansion of said tip portion, said expandable tip portion comprising an upper plate and a lower plate movable during expansion in opposite directions transverse to the axial direction of said elongate cage holder, said upper plate comprising an exterior surface having an outer contour matching said outer contour of said top surface and said lower plate comprising an exterior surface having an outer contour matching said outer contour of said bottom surface, the exterior surface of said upper plate and said lower plate projecting upon expansion of said expandable tip portion into a respective opening through said top surface and said bottom surface of said cage and lying no less than flush with said respective top surface and said bottom surface of said cage.

12. The apparatus of claim 11, wherein upon expansion of said expandable distal portion the exterior surface of said upper plate lies slightly above said top surface of said cage and the exterior surface of said lower plate lies slightly below said bottom surface of said cage.

13. The apparatus of claim 11, wherein the outer surface contour of said top surface is convex, and wherein the exterior surface of said upper plate has a convex outer contour substantially matching and lying flush with said outer contour of said top surface.

14. The apparatus of claim 13, wherein the outer surface contour of said bottom surface is convex, and wherein the exterior surface of said lower plate has a convex outer contour substantially matching and lying flush with said outer contour of said bottom surface.

15. The apparatus of claim 11, wherein said interbody fusion cage is sized and configured for anterior lumbar interbody fusion, wherein said distal end of said cage defines a posterior end and the proximal end defines an anterior end, and wherein the height at said anterior end is greater than the height at said posterior end.

16. A kit of parts for use in interbody fusion, comprising:
an inserter comprising an elongate cage holder, said cage holder comprising a proximal end and a distal end, the distal end terminating in an expandable tip portion comprising a connection surface for cooperative releasable engagement with an instrument engagement surface on an interbody fusion cage, said connection surface including a plurality of laterally extending, axially spaced grooves, each groove being configured to engage an instrument engagement surface on a different interbody fusion cage and being spaced from the distal end of said expandable tip portion by a different dimension; and a plurality of interbody fusion cages, each having a distal end and a proximal end, a distal end wall having an interior surface, a proximal opening though said proximal end, a hollow interior communicating with said distal end wall and said proximal opening, said hollow interior being sized and configured to receive said expandable tip portion of said cage holder such that a distal end of said expandable tip portion engages said interior surface, and an instrument engagement surface, each instrument engagement surface on a respective one of said cages being spaced from the interior surface of said posterior end wall of said cages at a predetermined distance correlated with the respective different dimensions that said inserter grooves are spaced from the distal end of said expandable tip portion, such that the instrument engagement surface of each cage is engageable with a different groove of said cage holder when said distal end of expandable tip portion is in engagement with said interior surface.

17. The kit of parts of claim 16, further comprising a modular plate sized and configured to attach to any one of said plurality of cages.

18. The kit of parts of claim 17, wherein each of said plurality of cages has a pocket at the anterior end of substantially the same size and configuration, and wherein said kit further includes a single modular plate configured to be received within the pocket of any of said plurality of cages for attachment to such cage.

19. The kit of parts of claim 18, wherein each of said plurality of cages is sized and configured for anterior lumbar interbody fusion, wherein said distal end of each of said cages defines a posterior end and the proximal end defines an anterior end, and wherein the height at said anterior end is greater than the height at said posterior end.

* * * * *